(12) United States Patent
Andree et al.

(10) Patent No.: US 6,562,759 B1
(45) Date of Patent: May 13, 2003

(54) SUBSTITUTED PHENYL URACILS

(75) Inventors: Roland Andree, Langenfeld (DE);
Mark Wilhelm Drewes, Langenfeld
(DE); Peter Dahmen, Neuss (DE);
Dieter Feucht, Monheim (DE); **Rolf
Pontzen**, Leichlingen (DE)

(73) Assignee: Bayer Aktiengesellschaft, Leverkusen
(DE)

( * ) Notice: Subject to any disclaimer, the term of this patent is extended or adjusted under 35 U.S.C. 154(b) by 0 days.

(21) Appl. No.: 10/030,673

(22) PCT Filed: Jul. 3, 2000

(86) PCT No.: PCT/EP00/06179

§ 371 (c)(1),
(2), (4) Date: Jan. 10, 2002

(87) PCT Pub. No.: WO01/05785

PCT Pub. Date: Jan. 25, 2001

(30) Foreign Application Priority Data

Jul. 14, 1999 (DE) .......................... 199 32 813

(51) Int. Cl.⁷ ...................... C07D 239/54; A01N 43/54
(52) U.S. Cl. ...................... 504/243; 544/309; 544/311; 544/312; 544/313; 544/314
(58) Field of Search .................... 504/243; 544/309, 544/311, 312, 313, 314

(56) References Cited

U.S. PATENT DOCUMENTS

| | | | |
|---|---|---|---|
| 4,812,164 A | 3/1989 | Wenger et al. | 71/92 |
| 4,859,229 A | 8/1989 | Wenger et al. | 71/92 |
| 4,979,982 A | 12/1990 | Brouwer et al. | 71/92 |
| 5,084,084 A | 1/1992 | Satow et al. | 71/92 |
| 5,116,404 A | 5/1992 | Ishii et al. | 71/92 |
| 5,127,935 A | 7/1992 | Satow et al. | 71/92 |
| 5,134,144 A | 7/1992 | Brouwer et al. | 514/274 |
| 5,154,755 A | 10/1992 | Satow et al. | 71/92 |
| 5,169,430 A | 12/1992 | Strunk et al. | 71/92 |
| 5,183,492 A | 2/1993 | Suchy et al. | 504/243 |
| 5,266,554 A | 11/1993 | Suchy et al. | 504/243 |
| 5,280,010 A | 1/1994 | Enomoto et al. | 504/243 |
| 5,356,863 A | 10/1994 | Satow et al. | 504/243 |
| 5,486,610 A | 1/1996 | Strunk et al. | 544/311 |
| 5,602,077 A | 2/1997 | Amuti et al. | 504/243 |
| 6,239,074 B1 | 5/2001 | Klintz et al. | 504/168 |
| 6,245,714 B1 | 6/2001 | Drewes et al. | 504/243 |

FOREIGN PATENT DOCUMENTS

| | | |
|---|---|---|
| EP | 542 685 | 5/1993 |
| WO | 95/06641 | 3/1995 |

Primary Examiner—John M. Ford
(74) Attorney, Agent, or Firm—Richard E. L. Henderson; John E. Mrozinski, Jr.

(57) ABSTRACT

The invention relates to novel substituted phenyluracils of the general formula (I)

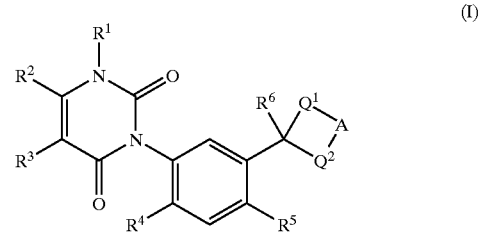

in which

A represents alkanediyl or alkenediyl, each of which has 2 to 5 carbon atoms and each of which is optionally substituted by cyano, halogen or by in each case optionally halogen- or $C_1$–$C_4$-alkoxy-substituted $C_1$–$C_4$-alkyl, $C_1$–$C_4$-alk-oxy-carbonyl or $C_2$–$C_4$-alkenyl or interrupted by O (oxygen), or represents cyclohexane-1,2-diyl or 1,2-phenylene, $Q^1$ represents O (oxygen) or S (sulphur), $Q^2$ represents O (oxygen) or S (sulphur), $R^1$ represents hydrogen, amino or optionally cyano-, halogen- or $C_1$–$C_4$-alkoxy-substituted alkyl having 1 to 4 carbon atoms, $R^2$ represents optionally halogen-substituted alkyl having 1 to 4 carbon atoms, $R^3$ represents hydrogen, halogen or optionally halogen-substituted alkyl having 1 to 4 carbon atoms, $R^4$ represents hydrogen, cyano, carbamoyl, thiocarbamoyl or halogen, $R^5$ represents cyano, carbamoyl, thiocarbamoyl or in each case optionally halogen-substituted alkyl or alkoxy having in each case 1 to 4 carbon atoms, and $R^6$ represents hydrogen or alkyl having 1 to 4 carbon atoms, and to a process for their preparation and to their use as herbicides.

8 Claims, No Drawings

SUBSTITUTED PHENYL URACILS

FIELD OF THE INVENTION

The invention relates to novel substituted phenyluracils, to processes for their preparation and to their use as herbicides.

BACKGROUND OF THE INVENTION

Certain substituted aryluracils are already known from the (patent) literature (cf. EP-A-255 047, EP-A-260 621, EP-A-408 382, EP-A-438 209, EP-A-473 551, EP-A-517 181, EP-A-542 685, EP-A-563 384, WO-A-91/00278, WO-A-91/07393, WO-A-93/06090, WO-A-93/14073, WO-A-95/06641, WO-A-97/45418, U.S. Pat. Nos. 4,979,982, 5,084, 084, 5,127,935, 5,154,755, 5,169,430, 5,486,610, 5,356, 863). However, these compounds have hitherto not attained any particular significance.

SUMMARY OF THE INVENTION

A substituted phenyluracil of the general formula (I)

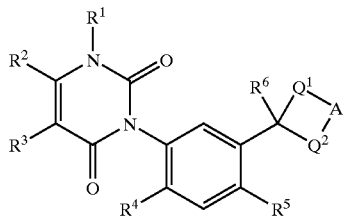

(I)

which has herbicidal activity.

DETAILED DESCRIPTION OF THE INVENTION

A represents alkanediyl or alkenediyl, each of which has 2 to 5 carbon atoms and each of which is optionally substituted by cyano, halogen or by in each case optionally halogen- or $C_1$–$C_4$-alkoxy-substituted $C_1$–$C_4$-alkyl, $C_1$–$C_4$-alkoxy-carbonyl or $C_2$–$C_4$-alkenyl or interrupted by O (oxygen), or represents cyclohexane-1,2-diyl or 1,2-phenylene, $Q^1$ represents O (oxygen) or S (sulphur), $Q^2$ represents O (oxygen) or S (sulphur), $R^1$ represents hydrogen, amino or optionally cyano-, halogen- or $C_1$–$C_4$-alkoxy-substituted alkyl having 1 to 4 carbon atoms, $R^2$ represents optionally halogen-substituted alkyl having 1 to 4 carbon atoms, $R^3$ represents hydrogen, halogen or optionally halogen-substituted alkyl having 1 to 4 carbon atoms, $R^4$ represents hydrogen, cyano, carbamoyl, thiocarbamoyl or halogen, $R^5$ represents cyano, carbamoyl, thiocarbamoyl or in each case optionally halogen-substituted alkyl or alkoxy having in each case 1 to 4 carbon atoms, and $R^6$ represents hydrogen or alkyl having 1 to 4 carbon atoms.

Preferred substituents or ranges of the radicals present in the formulae listed above and below are defined below.

A preferably represents ethane-1,2-diyl (dimethylene), propane-1,3-diyl (tri-methylene), ethene-1,2-diyl or propene-1,3-diyl, each of which is optionally substituted by cyano, fluorine, chlorine, bromine or by in each case optionally fluorine- and/or chlorine-, methoxy- or ethoxy-substituted methyl, ethyl, n- or i-propyl, methoxycarbonyl, ethoxycarbonyl, n- or i-propoxycarbonyl, ethenyl or propenyl or interrupted by O (oxygen), or represents cyclohexane-1,2-diyl or 1,2-phenylene.

$Q^1$ preferably represents O (oxygen).

$Q^2$ preferably represents O (oxygen).

$R^1$ preferably represents hydrogen, amino or in each case optionally cyano-, fluorine-, chlorine-, methoxy- or ethoxy-substituted methyl, ethyl, n- or i-propyl.

$R^2$ preferably represents in each case optionally fluorine- and/or chlorine-substituted methyl, ethyl, n- or i-propyl.

$R^3$ preferably represents hydrogen, fluorine, chlorine or in each case optionally fluorine- and/or chlorine-substituted methyl or ethyl.

$R^4$ preferably represents hydrogen, cyano, carbamoyl, thiocarbamoyl, fluorine, chlorine or bromine.

$R^5$ preferably represents cyano, carbamoyl, thiocarbamoyl or in each case optionally fluorine- and/or chlorine-substituted methyl, ethyl, methoxy or ethoxy.

$R^6$ preferably represents hydrogen, methyl or ethyl.

A particularly preferably represents in each case optionally fluorine-, chlorine-, methyl-, ethyl-, methoxycarbonyl- or ethoxycarbonyl-substituted ethane-1,2-diyl (dimethylene), propane-1,3-diyl (trimethylene) or ethene-1,2-diyl, or represents cyclohexane-1,2-diyl or 1,2-phenylene.

$R^1$ particularly preferably represents hydrogen, amino or methyl.

$R^2$ particularly preferably represents in each case fluorine- and/or chlorine-substituted methyl or ethyl.

$R^3$ particularly preferably represents hydrogen, fluorine, chlorine or optionally fluorine- and/or chlorine-substituted methyl.

$R^4$ particularly preferably represents hydrogen, fluorine or chlorine.

$R^5$ particularly preferably represents cyano, carbamoyl, thiocarbamoyl or in each case optionally fluorine- and/or chlorine-substituted methyl or methoxy.

$R^6$ particularly preferably represents hydrogen or methyl.

A very particularly preferably represents in each case optionally fluorine-, chlorine-, methyl-, ethyl-, methoxycarbonyl- or ethoxycarbonyl-substituted ethane-1,2-diyl (dimethylene) or propane-1,3-diyl (trimethylene).

$R^1$ very particularly preferably represents methyl.

$R^2$ very particularly preferably represents trifluoromethyl.

$R^3$ very particularly preferably represents hydrogen, chlorine or methyl.

$R^4$ very particularly preferably represents fluorine or chlorine.

$R^5$ very particularly preferably represents cyano or thiocarbamoyl.

$R^6$ very particularly preferably represents hydrogen.

The abovementioned general or preferred radical definitions apply both to the end products of the formula (I) and correspondingly to the starting materials or intermediates required in each case for the preparation. These radical definitions can be combined with one another as desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Saturated or unsaturated hydrocarbon radicals, such as alkyl or alkenyl, are—including in combination with heteroatoms, such as in alkoxy—in each case straight-chain or branched as far as this is possible.

Optionally substituted radicals can be mono- or polysubstituted, where in the case of polysubstitution the substituents can be identical or different.

The novel substituted phenyluracils of the general formula (I) have interesting biological properties. In particular, they have strong herbicidal activity.

The novel substituted phenyluracils of the general formula (I) are obtained when phenyluracils of the general formula (II)

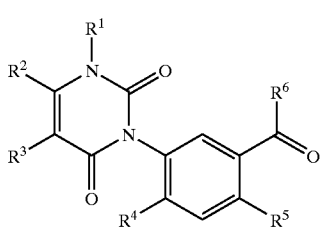

in which $R^1$, $R^2$, $R^3$, $R^4$, $R^5$ and $R^6$ are each as defined above, are reacted with dinucleophilic compounds of the general formula (III)

in which

A, $Q^1$ and $Q^2$ are each as defined above, if appropriate in the presence of a reaction auxiliary and if appropriate in the presence of a diluent, and subsequent reactions within the scope of the above definition of substituents are carried out, if appropriate, by customary methods on the resulting compounds of the general formula (I).

The compounds of the general formula (I) can be converted by customary methods into other compounds of the general formula (I) according to the above definition of substituents, for example by amination or alkylation (for example $R^1$: H→$NH_2$, H→$CH_3$), or else, for example, by reaction with hydrogen sulphide ($R^5$: CN→$CSNH_2$).

The compounds of the general formula (I) according to the invention in which $R^5$ represents cyano can in principle also be prepared according to the following formula scheme:

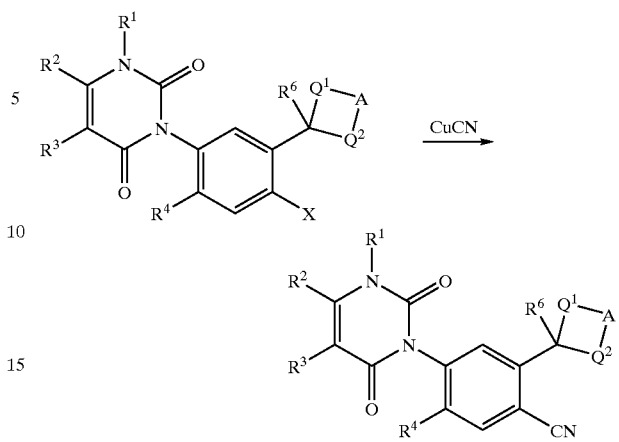

(X: halogen, in particular chlorine or bromine)

Using, for example, 1-(4-cyano-2-chloro-5-formylphenyl)-3,6-dihydro-2,6-dioxo-3-methyl-4-trifluoromethyl-1(2H)-pyrimidine and propane-1,3-diol as starting materials, the course of the reaction in the process according to the invention can be illustrated by the following formula scheme:

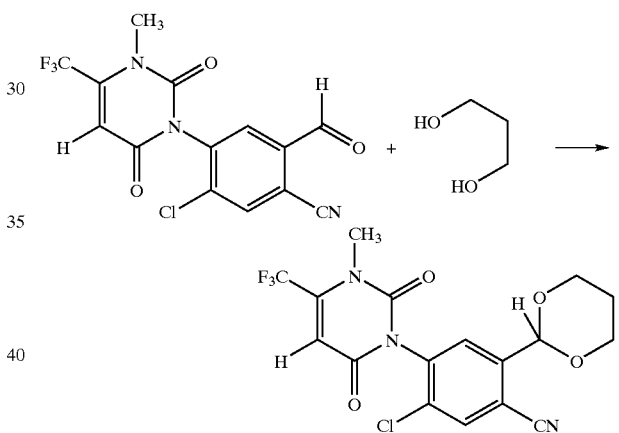

The formula (II) provides a general definition of the phenyluracils to be used as starting materials in the process according to the invention for preparing compounds of the general formula (I). In the general formula (II), $R^1$, $R^2$, $R^3$, $R^4$, $R^5$ and $R^6$ each preferably have those meanings which have already been mentioned above, in connection with the description of the compounds of the general formula (I) according to the invention, as being preferred, particularly preferred or very particularly preferred for $R^1$, $R^2$, $R^3$, $R^4$, $R^5$ and $R^6$.

The starting materials of the general formula (II) are known and/or can be prepared by processes known per se (cf. WO-A-97/45418).

The formula (III) provides a general definition of the dinucleophilic compounds further to be used as starting materials in the process according to the invention for preparing compounds of the general formula (I). In the general formula (III), A, $Q^1$ and $Q^2$ each preferably have those meanings which have already been mentioned above, in connection with the description of the compounds of the general formula (I) according to the invention, as being preferred, particularly preferred or very particularly preferred for A, $Q^1$ and $Q^2$.

The starting materials of the general formula (III) are known organic chemicals for synthesis.

The process according to the invention for preparing the compounds of the general formula (I) is, if appropriate, carried out in the presence of a reaction auxiliary. Suitable reaction auxiliaries in this case are preferably the customary condensation auxiliaries. An example of a particularly preferred condensation auxiliary which may be mentioned is chlorotrimethylsilane.

The process according to the invention for preparing the compounds of the general formula (I) is, if appropriate, carried out using a diluent. Suitable diluents for carrying out the process according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, and also sulphoxides, such as dimethyl sulphoxide.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—generally between 0.1 bar and 10 bar.

For carrying out the process according to the invention, the starting materials are generally employed in approximately equimolar amounts. However, it is also possible for one of the components to be used in a relatively large excess. The reaction is generally carried out in a suitable diluent in the presence of a reaction auxiliary, and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

Depending on the concentration, the active compounds according to the invention are suitable for total weed control, for example on industrial terrain and rail tracks and on paths and areas with and without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when used on the soil and on above-ground parts of plants. To a certain extent, they are also suitable for selective control of monocotyledonous and dicotyledonous weeds in monocotyledonous and dicotyledonous crops, both by the pre-emergence and by the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dyrnron, epropodan, EPTC, esprocarb, ethalfluralin, ethametsulfuron (-methyl), ethofumesate, ethoxyfen, ethoxysulfuron, etobenzanid, fenoxaprop(-P-ethyl), fentrazamide, flamprop (-isopropyl), flamprop(-isopropyl-L), flamprop(-methyl), flazasulfuron, florasulam, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen(-ethyl), flupoxaam, flupropacil, flurpyrsulfuron(-methyl, -sodium), flurenol(-butyl), fluridone, fluroxypyr(-meptyl), flurprimidol,
flurtamone, fluthiacet(-methyl), fluthiamide, fomesafen, glufosinate-(-ammonium), glyphosate(-isopropylammonium), halosafen, haloxyfop-(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop (-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

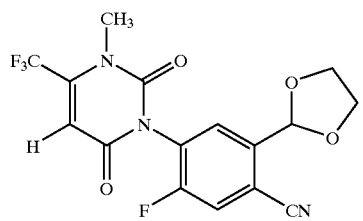

A mixture of 0.60 g (1.8 mmol) of 1-(4-cyano-2-fluoro-5-formyl-phenyl)-3,6-dihydro-2,6-dioxo-3-methyl-4- trifluoromethyl--(2H)-pyrimidine, 1 ml of ethane-1,2-diol, 0.9 ml of chlorotrimethylsilane and 20 ml of methylene chloride is stirred at room temperature (about 20° C.) for 18 hours. The mixture is then diluted with water, the organic phase is separated off, the aqueous phase is re-extracted with methylene chloride and the combined organic phases are dried with sodium sulphate and filtered. From the filtrate, the solvent is carefully distilled off under water-pump vacuum.

This gives 0.40 g (65% of theory) of 1-[4-cyano-2-fluoro-5-(1,3-dioxolan-2-yl)-phenyl]-3,6-dihydro-2,6-dioxo-3-methyl-4-trifluoromethyl-1(2H)-pyrimidine as a solid product.

$^1$H-NMR (D6-DMSO, δ): 6.58 ppm (s, 1H).

Analogously to Example 1, and in accordance with the general description of the preparation process according to the invention, it is also possible to prepare, for example, the compounds of the general formula (I) listed in Table I below.

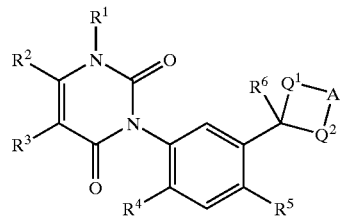

(I)

TABLE 1

Examples of the compounds of the formula (I)

| Ex. No. | $R^1$ | $R^2$ | $R^3$ | $R^4$ | R5 | $R^6$, $Q^1$, A, $Q^2$ group | Physical Data |
|---|---|---|---|---|---|---|---|
| 2 | $CH_3$ | $CF_3$ | H | F | CN | 1,3-dioxane (methyl) | |
| 3 | $CH_3$ | $CF_3$ | H | F | CN | 5,5-dimethyl-1,3-dioxane (methyl) | |
| 4 | $CH_3$ | $CF_3$ | H | F | CN | 4,7-dihydro-1,3-dioxepine (methyl) | |
| 5 | $CH_3$ | $CF_3$ | H | F | CN | benzo-1,3-dioxole (methyl) | |
| 6 | $CH_3$ | $CF_3$ | H | F | CN | 1,3-dithiolane (methyl) | |
| 7 | $CH_3$ | $CF_3$ | H | F | CN | 1,3-oxathiolane (methyl) | |
| 8 | $CH_3$ | $CF_3$ | H | F | $CSNH_2$ | 1,3-dioxolane (methyl) | |

TABLE 1-continued

Examples of the compounds of the formula (I)

| Ex. No. | R¹ | R² | R³ | R⁴ | R5 | $R^6 \underset{Q^2}{\overset{Q^1-A}{\bigvee}}$ | Physical Data |
|---|---|---|---|---|---|---|---|
| 9 | CH₃ | CF₃ | H | H | CN | tetrahydrofuran-dioxolane with CH₃ | |
| 10 | CH₃ | CF₃ | H | H | CSNH₂ | dioxolane with CH₃ | |
| 11 | CH₃ | CF₃ | Cl | F | CN | dioxolane with CH₃ | |
| 12 | CH₃ | CF₃ | CH₃ | F | CN | dioxolane with CH₃ | |
| 13 | CH₃ | CF₃ | H | F | CN | dioxolane with CH₃ and CH₃ | |
| 14 | CH₃ | CF₃ | H | F | CN | dioxolane with CH₃ and CH₂OCH₃ | |
| 15 | CH₃ | CF₃ | H | F | CN | hexahydrobenzodioxole with CH₃ | |

USE EXAMPLES

Example A

Pre-emergence Test

Solvent: 5 parts by weight of acetone

Emulsifier 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amount of active compound desired is applied per unit area. The concentration of the spray liquor is chosen so that the particular amount of active compound desired is applied in 1000 litres of water per hectare.

After three weeks, the degree of damage to the plants is rated in % damage in comparison to the development of the untreated control.

The figures denote:

0%=no effect (like untreated control)

100%=total destruction

In this test, for example, the compound of Preparation Example 1 shows very strong activity against weeds.

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:
0%=no effect (like untreated control)
100%=total destruction
In this test, for example, the compound of Preparation Example 1 shows very strong activity against weeds.

What is claimed is:

1. A phenyluracil of the formula (I)

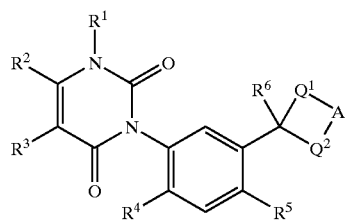

wherein
A represents alkanediyl or alkenediyl having 2 to 5 carbon atoms and optionally substituted by cyano, halogen or optionally halogen- or $C_1$–$C_4$-alkoxy-substituted $C_1$–$C_4$-alkyl, $C_1$–$C_4$-alkoxy-carbonyl or $C_2$–$C_4$-alkenyl or interrupted by O, or represents cyclohexane-1,2-diyl or 1,2-phenylene,
$Q^1$ represents O or S,
$Q^2$ represents O or S,
$R^1$ represents hydrogen, amino or optionally cyano-, halogen- or $C_1$–$C_4$-alkoxy-substituted alkyl having 1 to 4 carbon atoms,
$R^2$ represents optionally halogen-substituted alkyl having 1 to 4 carbon atoms,
$R^3$ represents hydrogen, halogen or optionally halogen-substituted alkyl having 1 to 4 carbon atoms,
$R^4$ represents hydrogen, cyano, carbamoyl, thiocarbamoyl or halogen,
$R^5$ represents cyano, carbamoyl, thiocarbamoyl or optionally halogen-substituted alkyl or alkoxy having 1 to 4 carbon atoms, and
$R^6$ represents hydrogen or alkyl having 1 to 4 carbon atoms.

2. The phenyluracil of claim 1, wherein
A represents ethane-1,2-diyl, propane-1,3-diyl, ethene-1,2-diyl or propene-1,3-diyl optionally substituted by cyano, fluorine, chlorine, bromine or by optionally fluorine- and/or chlorine-, methoxy- or ethoxy-substituted methyl, ethyl, n- or i-propyl, methoxycarbonyl, ethoxycarbonyl, n- or i-propoxycarbonyl, ethenyl or propenyl or interrupted by O, or represents cyclohexane-1,2-diyl or 1,2-phenylene,
$R^1$ represents hydrogen, amino optionally cyano-, fluorine-, chlorine-, methoxy- or ethoxy-substituted methyl, ethyl, n- or i-propyl,
$R^2$ represents optionally fluorine- and/or chlorine-substituted methyl, ethyl, n- or i-propyl,
$R^3$ represents hydrogen, fluorine, chlorine or optionally fluorine- and/or chlorine-substituted methyl or ethyl,
$R^4$ represents hydrogen, cyano, carbamoyl, thiocarbamoyl, fluorine, chlorine or bromine,
$R^5$ represents cyano, carbamoyl, thiocarbamoyl or optionally fluorine- and/or chlorine-substituted methyl, ethyl, methoxy or ethoxy, and
$R^6$ represents hydrogen, methyl or ethyl.

3. The phenyluracil of claim 1, wherein
A represents optionally fluorine-, chlorine-, methyl-, ethyl-, methoxycarbonyl- or ethoxycarbonyl-substituted ethane-1,2-diyl, propane-1,3-diyl or ethene-1,2-diyl, or represents cyclohexane-1,2-diyl or 1,2-phenylene,
$R^1$ represents hydrogen, amino or methyl,
$R^2$ represents fluorine- and/or chlorine-substituted methyl or ethyl,
$R^3$ represents hydrogen, fluorine, chlorine or optionally fluorine- and/or chlorine-substituted methyl,
$R^4$ represents hydrogen, fluorine or chlorine,
$R^5$ represents cyano, carbamoyl, thiocarbamoyl or optionally fluorine- and/or chlorine-substituted methyl or methoxy, and
$R^6$ represents hydrogen or methyl.

4. The phenyluracil of claim 1, wherein
A represents optionally fluorine-, chlorine-, methyl-, ethyl-, methoxycarbonyl- or ethoxycarbonyl-substituted ethane-1,2-diyl, propane-1,3-diyl,
$R^1$ represents methyl,
$R^2$ represents trifluoromethyl,
$R^3$ represents hydrogen, chlorine or methyl,
$R^4$ represents fluorine or chlorine,
$R^5$ represents cyano or thiocarbamoyl, and
$R^6$ represents hydrogen.

5. The phenyluracil of claim 1, wherein $Q^1$ represents O.

6. A method of making the phenyluracil of claim 1 comprising reacting a phenyluracil of the general formula (II)

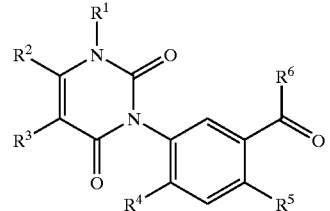

wherein $R^1$, $R^2$, $R^3$, $R^4$, $R^5$ and $R^6$ are each as defined above,
with a dinucleophilic compound of the formula (III)

wherein A, $Q^1$ and $Q^2$ are each as defined above.

7. An herbicidal composition comprising one or more phenyluracils of claim 1 and one or more extenders.

8. A method of controlling plant growth comprising applying an effective amount of one or more phenyluracils of claim 1 to a plant and/or its locus.

* * * * *